United States Patent [19]

Weaver

[11] 4,047,044

[45] Sept. 6, 1977

[54] ANODE HEAT MONITORING MEANS

[75] Inventor: Kenneth E. Weaver, Stamford, Conn.

[73] Assignee: The Machlett Laboratories, Inc., Stamford, Conn.

[21] Appl. No.: 691,945

[22] Filed: June 1, 1976

[51] Int. Cl.² .............................................. H05G 1/28
[52] U.S. Cl. ................................. 250/402; 250/416 R; 250/416 TV
[58] Field of Search ............ 250/416 R, 416 TV, 476, 250/401, 402

[56] References Cited

U.S. PATENT DOCUMENTS 3,062,960  11/1962  Laser ................................ 250/416 R
3,973,130  8/1976  Amemiya ............................ 250/476

Primary Examiner—Craig E. Church
Attorney, Agent, or Firm—John T. Meaney; Joseph D. Pannone; Harold A. Murphy

[57] ABSTRACT a radiographic system comprising an X-ray source disposed to direct an X-ray beam through a portion of a subject and produce an X-ray image thereof, imaging means for receiving the X-ray image and converting it into a visible image, sensing means for monitoring a parametric operating value of the source, and display means for showing the visible image and the parametric operating value in the same field of view.

5 Claims, 1 Drawing Figure

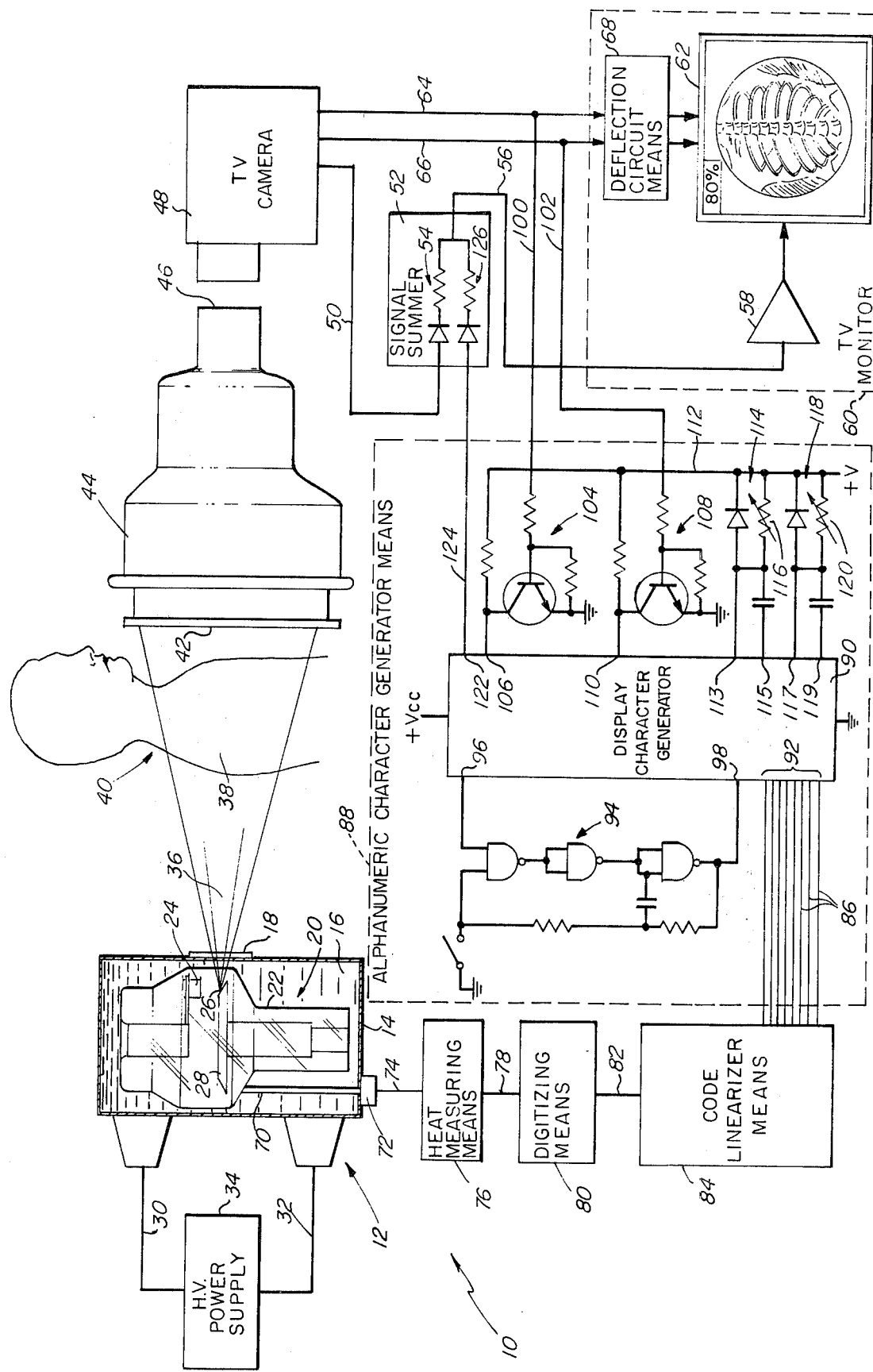

ANODE HEAT MONITORING MEANS

BACKGROUND OF THE INVENTION

1. Field of the Invention

This invention relates generally to radiographic systems and is concerned more particularly with a radiographic system having means for permitting an operator to monitor dynamic operation of the X-ray source while studying the output radiographic image.

2. Discussion of the Prior Art

A radiographic system generally includes an X-ray source disposed for directing an X-ray beam through a selected portion of a patient and transmitting an X-ray image thereof to a suitable image receptor. The image receptor may comprise an image converter, such as an image intensifier tube, for example, which receives the X-ray image and produces a corresponding output visible image. Thus, by suitable protective viewing means, such as television or optics, for examples, a radiologist may study the output visible image while the patient is being irradiated.

The X-ray source generally comprises an X-ray tube having an evacuated envelope wherein an electron emitting cathode is disposed for directing a beam of electrons onto a focal spot area of an anode target. In operation, the cathode supplies an electron current which is electrostatically focused onto the focal spot area by means of a high voltage impressed between the cathode and the anode. The electrostatically accelerated electrons impinge on the focal spot area with sufficient kinetic energy to generate the beam of X-rays which passes through the selected portion of the patient.

However, only about one percent of the input energy comprising the electron beam current and the electron accelerating voltage is converted into X-radiation. The remainder of the input energy is converted into thermal energy which greatly increases the temperature of the anode target. Generally, this thermal energy is stored in the mass of the anode and is dissipated by thermal radiation to the surrounding tube envelope. If the rate of increase in target temperature or the heat storage capacity of the anode exceed critical values, melting and cracking of anode target may occur, thereby reducing X-ray output and possibly rendering the tube inoperative.

Consequently, means have been developed for monitoring the temperature of the anode target during operation of the tube and indicating when the temperature is approaching a critical value. Thus, the X-ray tube may be deenergized temporarily to allow the anode to cool and thereby prolong the life of the tube. However, the temperature indicator of the monitoring means may be located in a position where it is not readily observable during an X-ray exposure, particularly when subdued illumination is required. Furthermore, during an X-ray exposure, the radiologist is primarily interested in the patient and, therefore, is concentrating on the output visible image. As a result, the anode target temperature may exceed the critical value, without being noticed, during the X-ray exposure.

Therefore, it is advantageous and desirable to provide a radiographic system with means for permitting a radiologist to monitor the anode target temperature while studying the output visible image produced by the radiographic system.

SUMMARY OF THE INVENTION

Accordingly, this invention provides a radiographic system comprising an X-ray source disposed to direct an X-ray beam through a portion of a patient and onto an image receptor having means for producing an output visible image of the irradiated portion, sensing means for monitoring the dynamic operating temperature of the source, and display means for showing the output visible image and the temperature of the source in the same field of view.

A preferred embodiment of this invention may comprise an X-ray tube having an evacuated envelope wherein an electron emitting cathode is disposed to direct a beam of electrons onto a focal spot area of a spaced anode target and generate an X-ray beam. The X-ray beam is directed onto an input faceplate of an image intensifier tube which produces a corresponding visible image on an output faceplate thereof. A television camera tube is disposed to receive the output visible image and transmit a corresponding electron image to a suitable display terminal. Heat measuring means is operatively coupled to the anode target of the X-ray tube for determining the temperature thereof and transmitting a suitable signal to the display terminal. As a result, the output visible image and the temperature of the anode target are displayed on the output screen of the display terminal.

BRIEF DESCRIPTION OF THE DRAWING

For a better understanding of this invention, reference is made in the following more detailed description to the accompanying drawing wherein:

FIG. 1 is a schematic view of a radiographic system embodying the invention.

DESCRIPTION OF THE PREFERRED EMBODIMENT

Referring to the drawing, FIG. 1 shows a radiographic system 10 including an X-ray generator 12 comprised of a shielded housing 14 filled with a dielectric fluid 16 and having an X-ray transparent port 18. Supported in the fluid 16 is an X-ray tube 20 of the rotating anode type having an evacuated enevelope 22. Within envelope 22, a cathode 24 is disposed in spaced aligned relationship with a focal spot area 26 on a sloped surface of a rotatable anode target disc 28. The cathode 24 and the anode disc 28 are electrically connected through respective cables 30 and 32 to a high voltage power supply 34.

In operation, the cathode 24 is heated electrically to emit an electron beam current which is electrostatically focused onto the focal spot area 26 of the rotating anode target disc 28. As a result, the electrostatically accelerated electrons in the beam impinge on the focal spot area 26 with sufficient kinetic energy to generate X-rays in the target material. Consequently, an X-ray beam 36 emanates from the focal spot area 26 and passes through the X-ray transparent port 18 of housing 14. The X-ray beam 36 may be directed through a selected portion 38 of a patient 40 interceptingly disposed in the path of the beam 36.

After passing through the selected portion 38, the X-ray beam 36 is modified correspondingly and conveys an X-ray image of the internal structure in portion 38 to an X-radiation transparent input faceplate 42 of an image intensifier tube 44. The image intensifier tube 44 may be of the conventional cylindrical type, such as disclosed in U.S. Pat. No. 3,417,242 granted to R. W. Windebank and assigned to the assignee of this invention, for example. Accordingly, the image intensifier tube 44 converts the incident X-ray image into an equivalent electron image which is amplified and focused on an imaging screen (not shown) adjacent a transparent output faceplate 46 of tube 44. As a result, the amplified electron image produces a bright visible image which is viewable through the output faceplate 46.

Optically coupled to the output faceplate 46 is a suitable electronic TV camera unit 48, such as Model No. 4TE26A1H made by General Electric Company of Syracuse, N.Y., for example. The TV camera 48 receives the output visible image produced by image intensifier tube 44 and converts it, as by an electron beam scanning a raster pattern on a storage target (not shown), for example, into a train of sequential video signals. These video signals are conducted out of camera tube 48 and pass through an external conductor 50 to a signal summer means 52. Within the signal summer 52, the video signals may pass through a series connected diode and resistor network 54, to an external output conductor 56. The conductor 56 is connected to a video amplifier 58 in a suitable TV monitor unit 60, such as Model No. SNA/C made by Conrac Corporation of Covina, Calif., for example. In the TV monitor unit 60, the output of video amplifier 58 is connected to an appropriate input terminal of a TV picture tube 62 which displays an enlarged visual image of the image produced by intensifier tube 44. Since the image displayed by the TV monitor unit 62 corresponds to the irradiated position 38 of the patient 40, it is this image which is studied in order to diagnose the patient's condition.

Also produced, in a well known manner, within TV camera 48 are respective horizontal and vertical synchronizing signals which generally are associated with the raster scanning pattern of the electron beam within the TV camera 48. The horizontal and vertical synchronizing signals are conducted out of TV camera 48 and pass through respective external conductors 64 and 66 to a deflection circuit means 68 in the TV monitor unit 60. The deflection circuit means 68 is suitably connected to the picture tube 62 for timing a scanning electron beam therein (not shown) to produce a raster pattern corresponding to the raster pattern scanned by the electron beam in TV camera 48. However, since the raster pattern scanned by the electron beam in picture tube 64 is rectangular and the output faceplate 46 of intensifier tube 44 is cylindrical, there are four unused corner portions in the display screen of picture tube 64. Accordingly, parametric operating values of the x-ray tube 20 may be displayed in any one of the unused corner portions without interfering with the image produced by intensifier tube 44. Thus, a parametric operating value will be displayed in the same field of view as the image of the irradiated portion 38, where the attention of the operator is concentrated.

Optically coupled to the rotating anode target 20 is one end of a fiber optic bundle 70 comprising a radiation transmitting means for conducting infrared radiation received from the anode target 28 out of the generator 12. The fiber optic bundle 70 may have one end suitably affixed, as by epoxy bonding, for example to a portion of envelope 22 adjacent the sloped surface of anode target 28, and extends hermetically through the housing 14 of generator 12 to terminate in an opposing output end which is aligned with a suitable infrared detector means 72. The detector means 72 may comprise, for example, a germanium photodiode which is sensitive to infrared radiation and generates an electrical output signal corresponding to the temperature of anode target 28. The electrical output signal produced by the detector means 72 passes through an external conductor 74 to a heat measuring means 76, such as Heat Sensor Readout Model No. S-56987 made by Machlett Laboratories, Incorporated, a subsidiary of Raytheon Company, Lexington, Mass., for example. The heat measuring means 76 may be provided with a logarithmic amplifier (not shown) which converts the signal produced by the infrared detector means 72 into a measured percentage value of the heat storage capacity of the anode target 26. Thus, there is provided a parametric value sensing means comprising infrared transmitting means 70 having an output coupled to an infrared detecting means 72 which, in turn, is connected to a heat measuring means 76.

The logarithmic output signal produced by the heat measuring means 76 flows through an external conductor 78 to a digitizing means 80, such as Analog-to-Digital Converter Model No. 535-12A made by Hybrid Systems of Burlington, Mass., for example. The digitizing means 80 receives the logarithmic signal produced by the heat measuring means 76 and converts it, as by voltage to frequency conversions, for example, into a train of discrete signals which correspond to the logarithmic input signal. This train of discrete signals flows through an external conductor 82 to a code linearizer means 84, such as PROM Model No. HM-7640 made by Harris Semiconductor Division of Harris Corporation, Melbourne, Fla., for example. The code linearizer means converts the logarithmically related discrete signals into a corresponding linear series of discrete signals and produces suitable binary coded output signals. The binary coded output signals may comprise, for example, two groups of four discrete signals, each group being associated with a respective digit of the percentage parametric value produced by the heat measuring means 76.

The binary coded signals produced by the code linearizer means 84 flow through respective external conductors 86 to respective input terminals of an alphanumeric character generator means 88. The character generator means 88 may comprise a suitable integrated circuit module 90, such as Display Character Generator Model No. MM5841 made by National Semiconductor Corporation of Santa Clara, Calif., for example. The module 90 is provided with respective input terminals 92 having applied thereto the binary coded signals produced by the code linearizer means 84. The character generator means 88 also may include a suitable clock-oscillator circuit 94 which is electrically connected between an OSCILLATOR INHIBIT terminal 96 and a CLOCK terminal 98 of the integrated circuit module 90. Counters (not shown) are incorporated in the integrated circuit module 90 and are operated by the clock-oscillator circuit 94 to keep track of the time slots in the display produced by television monitor 60.

The horizontal and vertical synchronizing signals passing through respective conductors 64 and 66 to the deflector circuits 68 also flow through connecting conductors 100 and 102, respectively, to the character generating means 88. Within the generating means 88, the conductor 100 is connected through an inverter-amplifier input circuit means 104 to a respective input terminal 106 of the integrated circuit module 90. Similarly, the conductor 102 is connected through another inverter-amplifier input circuit means 108 to a respective input terminal 110 of integrated circuit module 90. The inverter-amplifier input circuit means 104 and 108 serve to supply the horizontal and vertical synchronizing signals, respectively, to the integrated circuit module 90 at the polarity and amplitude required for proper functioning thereof. Each of the input terminals 106 and 110 are resistively connected to a V+ terminal lead 112. The V+ terminal lead 112 also is connected to a horizontal positioning circuit means 114 which is connected across respective input terminals 113 and 115 of the module 90, and includes an adjustable resistor 116 for varying the RC time constant of the circuit means 114. Similarly, the V+ terminal lead 104 is connected to a vertical positioning circuit means 118 which is connected across respective input terminals 117 and 119 of the module 90, and includes an adjustable resistor 120, for varying the RC time constant of the circuit means 118.

An output terminal 122 of the module 90 is connected through an external conductor 124 to the signal summer means 52 wherein it is connected through a series connected diode-resistor network 126 to the output conductor 56. Thus, the parametric character signals produced by the generator means 88 are combined with the video signals produced by TV camera tube 48 and pass through conductor 56 to the video amplifier 58 in TV monitor unit 60. As a result, the measured percentage value of the heat storage capacity of anode target 28 is shown on the display screen of picture tube 62 along with the image produced by intensifier tube 44. By varying the resistors 116 and 120 in the horizontal and vertical positioning circuit means, 114 and 118, respectively, the position of the measured percentage value may be adjusted to occupy any portion of the display screen of picture tube 62 desired. Therefore, the respective resistors may be adjusted to display the measured percentage value of anode heat storage capacity in one of the unused corners, such as the upper left-hand corner, for example, of the raster pattern on the display screen of picture tube 62. In this manner, the measured parametric value of anode heat storage capacity may be shown in the same field of view as the diagnostic image of the irradiated portion 38 of patient 40. Consequently, the diagnostician may concentrate on the image of irradiated portion 38 while observing the measured parametric operating value of x-ray tube 20. Accordingly, if the measured parametric value is seen to approach a critical level, the x-ray tube 20 may be deenergized before irreparable damage occurs.

Although the displayed parametric value has been described as the measured percentage value of allowable heat storage capacity, other information, such as anode target temperature, electron current flow, anode-to-cathode peak voltage, for examples, may be similarly displayed. Thus, a photograph taken of the display screen of TV monitor 60 may bear pertinent information regarding the conditions under which the radiographic image on the display screen was produced. Furthermore, although the measured parametric value has been described as varying logarithmically, it may equally well vary linearly and may be measured as a series of pulses, whereby the subsequent digitizing and linearizing means may not be required.

From the foregoing, it will be apparent that all of the objectives of this invention have been achieved by the structures shown and described herein. It also will be apparent, however, that various changes may be made by those skilled in the art without departing from the spirit of the invention as expressed in the appended claims. It is to be understood, therefore, that all matter shown and described herein is to be interpreted as illustrative and not in a limiting sense.

What is claimed is:

1. A radiographic system for displaying a visible image of an irradiated subject and comprising:
    an x-ray source disposed to direct an x-ray beam through the subject and produce a corresponding x-ray image thereof;
    imaging means interceptingly disposed in the path of the x-ray beam for receiving the x-ray image and producing a corresponding visible image;
    sensing means disposed to receive informational data concerning the x-ray source and produce equivalent electrical signals; and
    display means comprising a television monitor with a display screen and a television camera unit disposed to receive the visible image, said monitor being electrically coupled the camera unit and the sensing means for showing the visible image and the informational data in the same field of view on the display screen.

2. A radiographic system as set forth in claim 1 wherein the display means includes binary coding means connected to the sensing means for converting the equivalent electrical signals therefrom into binary coded signals.

3. A radiographic system as set forth in claim 2 wherein the display means includes alphanumeric character generator means connected to the binary coding means for converting the binary coded signals into corresponding character video signals.

4. A radiographic system as set forth in claim 3 wherein the display means includes signal summer means connected between the television camera unit and the alphanumeric character generator means for displaying the character video signals on the display screen of the television monitor simultaneously with image video signals.

5. A radiographic system as set forth in claim 4 wherein the alphanumeric character generator means includes adjusting circuit means for varying the position of the character video signals on the display screen of the television monitor.

* * * * *